United States Patent [19]

Onda et al.

[11] 4,385,078
[45] May 24, 1983

[54] METHOD FOR PROVIDING ENTERIC COATING ON SOLID DOSAGE FORMS AND AQUEOUS COMPOSITIONS THEREFOR

[75] Inventors: Yoshiro Onda, Niigata; Hiroaki Muto, Joetsu; Hiroshi Suzuki, Niigata; Kazumasa Maruyama, Joetsu; Atsushi Hatayama, Niigata, all of Japan

[73] Assignee: Shin-Etsu Chemical Co., Ltd., Tokyo, Japan

[21] Appl. No.: 71,298

[22] Filed: Aug. 30, 1979

[30] Foreign Application Priority Data

Sep. 4, 1978 [JP] Japan ................. 53-108269

[51] Int. Cl.$^3$ ............................ C08L 1/10; C08L 1/14
[52] U.S. Cl. ................................ 427/3; 424/35; 106/170; 106/178; 106/180; 106/188; 106/189; 106/197 R
[58] Field of Search ................... 106/197 R, 178, 189, 106/180, 170, 198, 188; 424/35; 427/3

[56] References Cited

U.S. PATENT DOCUMENTS

| | | | |
|---|---|---|---|
| 2,716,615 | 8/1955 | Voris | 106/189 |
| 2,843,583 | 7/1958 | Voris | 536/66 |
| 3,406,031 | 10/1968 | Lee | 106/171 |
| 3,629,237 | 12/1971 | Koyanagi et al. | 106/197 R |
| 3,899,439 | 8/1975 | Mahlman | 106/197 R |
| 3,935,326 | 1/1976 | Groppenbacher | 427/3 |
| 4,287,221 | 9/1981 | Tonedacki et al. | 427/3 |
| 4,330,338 | 5/1982 | Banker | 106/170 |

FOREIGN PATENT DOCUMENTS

WO80/00659 4/1980 PCT Int'l Appl. .

Primary Examiner—Allan Lieberman
Assistant Examiner—Patricia Short
Attorney, Agent, or Firm—Toren, McGeady and Stanger

[57] ABSTRACT

A novel aqueous coating composition is proposed for providing enteric coating on solid dosage forms such as tablets. The aqueous coating composition of the invention comprises a fine powder of an enterosoluble cellulose derivative such as hydroxypropylmethylcellulose phthalate and hydroxypropylmethylcellulose acetate succinate, which is insoluble in water but can be plasticized and solubilized with certain plasticizing agents, as dispersed in an aqueous dispersing medium and a plasticizing agent having compatibility with the enterosoluble cellulose derivative and dissolved in the aqueous dispersing medium. The particle size of the enterosoluble cellulose derivative and the boiling point of the plasticizing agent is the key parameters and should be finer than 100 μm in an average particle diameter and not lower than 100° C., respectively. Upon application of the aqueous coating composition to the solid dosage forms, water as the dispersing medium is first evaporated leaving the cellulose derivative and the plasticizing agent, which latter solubilizes the former to form a continuous coating layer on the solid dosage forms imparting good and satisfactory enterosolubility thereto.

12 Claims, No Drawings

METHOD FOR PROVIDING ENTERIC COATING ON SOLID DOSAGE FORMS AND AQUEOUS COMPOSITIONS THEREFOR

BACKGROUND OF THE INVENTION

The present invention relates to a method for providing enteric coating on solid dosage forms and aqueous coating compositions therefor.

As is well known, certain solid dosage forms are desired to be disintegrated only when they arrive at the intestinal canals upon oral administration and they are imparted with enterosoluble property by providing so-called enteric coating on the surface.

Known enteric coating compositions in the prior art are, for example, prepared by dissolving certain cellulose derivatives such as cellulose acetate phthalate, hydroxypropylmethylcellulose phthalate and the like in a suitable organic solvent to form an organic solution.

These enteric coating compositions in the form of organic solutions have several defects. For example, in the first place, they are undesirable because of the relatively high production cost due to the use of large volumes of organic solvents. Further, there can be problems from the standpoints of safety and environmental pollution since the use of an organic solvent is not free from the danger of fire or explosion in the course of the coating process and emission of the vapor of the organic solvents to the atmosphere causes a difficult problem of environmental pollution. In addition, any traces of the organic solvents remaining in the coating layer on the solid dosage forms are undesirable in consideration of possible toxicity of them.

It is therefore an important problem in the pharmaceutics to develop an aqueous enteric coating composition with wide versatility for various kinds of solid dosage forms and free from the above described problems in the prior art compositions of organic solution type for enteric coating.

Recently, several methods have been proposed for providing enteric coating on solid dosage forms by use of aqueous coating compositions (see, for example, Japanese Patent Publication No. 53-12569 and Japanese Patent Kokai No. 53-96314) but these methods have also some problems of their own.

SUMMARY OF THE INVENTION

It is therefore an object of the present invention to provide a novel method for enteric coating on various solid dosage forms by use of an aqueous coating composition and to provide an aqueous coating composition suitable for the purpose.

The aqueous enteric coating composition according to the present invention comprises particles of an enterosoluble cellulose derivative having an average particle diameter not exceeding 100 $\mu$m, where more than 95% by weight of the particles have a diameter of 150 $\mu$m or smaller, as dispersed in water or in an aqueous medium containing a plasticizing agent having compatibility with the cellulose derivative and a boiling point of 100° C. or higher or, preferably, 110° C. or higher.

DETAILED DESCRIPTION OF THE PREFERRED EMBODIMENTS

Extensive investigations have been undertaken by the inventors with an object to solve the above described problems in the prior art enteric coating compositions leading to the establishment of a novel method for providing enteric coating on various solid dosage forms and an aqueous enteric coating composition as described above suitable for practicing the objective method.

The enterosoluble cellulose derivatives to be dispersed in water or in an aqueous medium as the dispersing medium are not limited to particular ones but may be any one of known cellulose derivatives derived from various kinds of alkyl ethers of cellulose, hydroxyalkyl ethers of cellulose, monocarboxylic acid esters of cellulose and mixed cellulose ester ethers with a combination of two or more of alkyl, hydroxyalkyl and monocarboxyl groups by monoesterification with a dibasic or tribasic carboxylic acid.

The above mentioned alkyl and hydroxyalkyl ethers of cellulose are exemplified by methylcellulose, ethylcellulose, hydroxyethylcellulose, hydroxypropylcellulose, hydroxybutylcellulose, hydroxyethylethylcellulose, hydroxypropylmethylcellulose, hydroxybutylmethylcellulose and the like and the monocarboxylic acid esters of cellulose are exemplified by the esters of cellulose with acetic acid, butyric acid, propionic acid and the like. The dibasic and tribasic acids are exemplified by phthalic acid, tetrahydrophthalic acid, trimellitic acid, maleic acid, succinic acid, glutaric acid and the like, of which the dibasic acids are preferred to the tribasic.

Thus, some of the examples of the enterosoluble cellulose derivatives suitable for use in the present invention are hydroxypropylmethylcellulose phthalate, cellulose acetate phthalate, hydroxypropylmethylcellulose acetate succinate, hydroxypropylcellulose phthalate and the like.

As is described above and undermentioned in further detail, these enterosoluble cellulose derivatives are used as dispersed in water or an aqueous medium to form an aqueous enteric coating composition so that the maximum particle size or the particle size distribution of the cellulose derivative is an important parameter. For example, coarser particles may give no stable aqueous dispersion and cause jamming of the nozzles of the spray gun used in the coating process. Further, coarser particles cannot be readily plasticized by the plasticizing agent contained in the dispersing medium bringing about a difficulty in forming satisfactory enteric coating films on the solid dosage forms. In this connection, the particle size distribution of the enterosoluble cellulose derivative should desirably be such that at least 95% by weight of the particles have a diameter of 150 $\mu$m or smaller or, preferably, of 100 $\mu$m or smaller.

The enterosoluble cellulose derivatives with particle size distribution as described above can be obtained by the pulverization of an ordinary product, which is performed in various procedures not limited to any particular ones including dry processes and wet processes although dry processes are preferred when larger stability of the enterosoluble cellulose derivative in storage is desired before it is dispersed in the aqueous dispersing medium.

In the next place, the plasticizing agent contained in the aqueous dispersing medium serves to plasticize and solubilize the enterosoluble cellulose derivative when the water or the aqueous medium in the coating composition has been evaporated to dryness on the surface of the solid dosage form leaving the particles of the enterosoluble cellulose derivative and the plasticizing agent as solvent-free to form a continuous coating film on the particles of the solid dosage form.

The plasticizing agents capable of functioning as described above are exemplified by monoacetins, diacetins, triacetin, glycerine, ethyleneglycol monomethyl ether, ethyleneglycol monoethyl ether, propyleneglycol, polyethleneglycol, benzyl alcohol, diacetone alcohol, ethyl lactate and the like. These compounds may, of course, be used either singly or as a combination of two or more.

The amount of the above named plasticizing agents in the aqueous dispersing medium depends upon several parameters such as the kind of the plasticizing agent, kind and particle size distribution of the enterosoluble cellulose derivative and others. Usually, the amount should be at least 5% or, preferably, at least 10% by weight based on the amount of the enterosoluble cellulose derivative with the upper limit at around 200% by weight.

The above named plasticizing agents all have a boiling point of 100° C. or higher since premature evaporation of the plasticizing agent with a boiling point lower than 100° C. leads to insufficient plasticization and solubilization of the particles of the enterosobuble cellulose derivative on the surface of the solid dosage forms when the aqueous coating composition is applied thereto and dried.

The dispersing medium for the enterosoluble cellulose derivative is prepared by merely dissolving desired amount of the plasticizing agent in water when the plasticizing agent has a good solubility in water. When the plasticizing agent is less soluble in water, however, it can be solubilized by adding certain water-soluble organic solvents such as acetone and ethyl alcohol to the water or by being admixed with small amount of the above mentioned water-soluble plasticizing agent such as diacetins and ethyleneglycol monomethyl ether. In addition, it is also a possible way to emulsify a plasticizing agent with little solubility in water by admixing water-soluble organic solvents as mentioned above, if necessary, by the aid of a surface active agent.

The powder of the enterosoluble cellulose derivative is added to the water or the aqueous medium containing the plasticizing agent and dispersed uniformly by a suitable mechanical mixing means such as a ball mill, homomixer and the like to give the aqueous coating composition of the present invention for providing enteric coating on solid dosage forms. The amount of water as the dispersing medium for dispersing the enterosoluble cellulose derivative is usually in the range from 200 to 2,000% by weight of the cellulose derivative. When the amount of the dispersing medium is larger than 2,000% by weight, the resultant coating composition requires an excessive drying time after application of the composition to the solid dosage forms while smaller amount of water than 200% by weight gives an increased consistency of the resultant coating composition which can be applied to the solid dosage forms only with difficulty. It is of course optional that the coating composition is stored with a high solid content and diluted with water to a suitable solid content directly before use.

The aqueous coating composition of the present invention may contain several kinds of conventional additives such as protective colloids, coloring agents, sweetenings, flavorings and the like. In particular, the addition of a protective colloid is sometimes advantageous by increasing the thixotropy of the resultant coating composition which in turn prevents the separation of the dispersing medium and the dispersant particles to facilitate the spraying process in the coating operation and also to decrease cracks in the coating films produced by drying after application.

Preferred protective colloids for such a purpose are exemplified by water-soluble cellulose ethers such as hydroxypropylmethylcellulose, hydroxyethylcellulose and the like having a viscosity of about 100 to 10,000 centipoise at 20° C. as measured in a 2% by weight aqueous solution. The amount of these protective colloids is usually in the range from 0.05 to 5.0% by weight of the amount of the entrosoluble cellulose derivative in order to fully exhibit the above described advantages.

The process of coating of solid dosage forms with the thus prepared aqueous coating composition is rather conventional and any known coating means such as pan-coating, fluidized coating and the like can be applied. It is of course optional that the solid dosage forms, e.g. tablets, as the objective material of the inventive method have been provided with a suitable undercoating with shellac, hydroxypropylmethylcellulose or the like which is conventionally undertaken as the undercoating for sugar coating.

Following are the examples and comparative examples to illustrate the present invention in further detail, in which parts are all given by parts by weight. In the examples, the average number of the substituent groups and the degree of substitution per glucose unit of the cellulose derivatives are expressed by M.S. and D.S., respectively. The testing procedures for the solubility in the McIlvaine's buffer solutions and the disintegration time in the artificial gastric juice (the first solution) and in the artificial intestinal juice (the second solution) were as follows.

Solubility test in McIlvaine's buffer solutions:

A film of about 0.1 mm thickness prepared by casting on a glass plate and drying at 50° C of the aqueous coating composition was cut into square pieces of 10 mm × 10 mm wide and a piece of the film was placed in a disintegration tester for tablets according to the Ninth Revised Japanese Pharmacopoeia into which a McIlvaine's buffer solution with a pH value of 4.5, 5.0, 5.5 or 6.0 was passed at 37±2° C. and the time for complete disappearance of the piece was recorded in minutes.

Disintegration time in artificial gastric and intestinal juices:

Tablets of a mixture of lactose and starch each weighing 250 mg were coated with the inventive enteric coating composition in a coating amount of 25 mg per tablet. The coated tablet was put in the artificial gastric juice with a pH of 1.2 (the first solution) or in the artificial intestinal juice with a pH of 7.5 (the second solution) contained in the disintegration tester as used in the solubility test above and the time for disintegration of the tablet was recorded in minutes.

EXAMPLE 1

A hydroxypropylmethylcellulose phthalate (hereinafter abbreviated as HPMCP) having a M.S. value for the hydroxypropoxy groups of 0.27, a D.S. value for the methoxy groups of 1.85 and a D.S. value for the phthalyl groups of 0.72 was comminuted in a jet mill into a fine powder having an average particle diameter of about 10 μm where more than 95% by weight of the particles had a particle diameter of about 30 μm or smaller.

On the other hand, 0.15 part of α,α'-diacetin and 0.001 part of a hydroxypropylmethylcellulose (90SH-4000, a product of Shin-Etsu Chemical Co., Japan) were dissolved in 4.0 part of water, into which 1.0 part of the above prepared fine powder of the HPMCP was added and dispersed to give a milky white aqueous coating composition by shaking in a porcelain ball mill rotated for 30 minutes.

The thus prepared aqueous coating composition was shaped into a translucent film of about 0.1 mm thickness in a manner as described above as the test specimen for the solubility test and, in parallel, lactose-starch tablets were coated with this aqueous coating composition by the spray method to give coated tablets with a coating amount of 25 mg per tablet.

The results of the solubility test and the disintegration test undertaken with the film and the coated tablets were as follows.

Solubility in McIlvaine's buffer solutions:
8 to 10 minutes for the solution with a pH of 6.0;
10 to 14 minutes for the solution with a pH of 5.5;
100 to 120 minutes for the solution with a pH of 5.0; and not dissolved within 2 hours in the solution with a pH of 4.5.

Disintegration time:
not disintegrated within 2 hours in the first solution; and
4 to 6 minutes in the second solution.

EXAMPLE 2

The same HPMCP as used in Example 1 was comminuted in a high-speed hammer mill to a fine powder having an average particle diameter of about 20 μm where more than 95% by weight of the particles had a particle diameter of about 50 μm or smaller.

The preparation of the aqueous coating composition with the thus obtained fine powder of the HPMCP was carried out in just the same manner as in Example 1 and the solubility test and the disintegration test undertaken with the film and the coated tablets gave the results as shown below.

Solubility in McIlvaine's buffer solutions:
6 to 8 minutes for the solution with a pH of 6.0;
8 to 10 minutes for the solution with a pH of 5.5;
60 to 80 minutes for the solution with a pH of 5.0; and not dissolved within 2 hours in the solution with a pH of 4.5.

Disintegration time:
not disintegrated within 2 hours in the first solution; and
3 to 5 minutes in the second solution.

COMPARATIVE EXAMPLE 1

The same experimental procedure as in Example 2 was repeated except that the comminution of the HPMCP with the high-speed hammer mill gave a powder having an average particle diameter of about 105 μm where about 10% by weight of the particles had a particle diameter of about 150 μm or larger.

The film shaped with the thus prepared aqueous coating composition was cloudy with fissures and the coating composition was found not suitable for spray coating of tablets because of the frequent blockage of the spray nozzles and appearance of dusting on the surface of the coated tablets.

COMPARATIVE EXAMPLE 2

The same experimental procedure as in Example 1 was repeated except that the aqueous dispersing medium was prepared by dissolving 1.0 part of ethyl alcohol, 0.1 part of methylene chloride and 0.001 part of the same hydroxypropylmethylcellulose as in Example 1 in 4.0 part of water.

The milky white aqueous coating composition prepared with the above dispersing medium was cast on a glass plate and dried at 50° C. but no smooth and continuous film was obtained with many of the unsolubilized particles of the cellulose derivative remaining as particles. The coating of the lactose-starch tablets tried with the thus prepared aqueous coating composition was quite unsuccessful with remarkable dusting on the tablets.

EXAMPLE 3

A cellulose acetate phthalate having a D.S. value for the acetyl groups of 1.94 and a D.S. value for the phthalyl groups of 0.92 was comminuted in a jet mill into a fine powder having an average particle diameter of about 10 μm where more than 95% by weight of the particles had a particle diameter of about 30 μm or smaller.

On the other hand, a dispersing medium was prepared by dissolving 0.05 part of triacetin and 0.05 part of α,α'-diacetin in 4.0 parts of water and 1.0 part of the above pulverized cellulose acetate phthalate was added and dispersed therein by shaking in a porcelain ball mill rotated for 30 minutes to give a milky white aqueous coating composition.

The solubility test for the translucent film shaped with the coating composition and the disintegration test for the tablets coated therewith gave the results as follows.

Solubility in McIlvaine's buffer solutions:
10 to 14 minutes for the solution with a pH of 6.0;
20 to 30 minutes for the solution with a pH of 5.5; not dissolved within 2 hours in the solutions of a pH of 5.0 or 4.5.

Disintegration time:
not disintegrated within 2 hours in the first solution; and
6 to 8 minutes in the second solution.

EXAMPLE 4

A hydroxypropylmethylcellulose acetate succinate (hereinafter abbreviated as HPMCAS) having a M.S. value for the hydroxypropoxy groups of 0.27, a D.S. value for the methoxy groups of 1.85, a D.S. value for the acetyl groups of 0.43 and a D.S. value for the succinyl groups of 0.43 was comminuted in a vibration ball mill into a fine powder having an average particle diameter of about 30 μm where more than 95% by weight of the particles had a particle diameter of about 50 μm or smaller.

The dispersing medium was prepared by dissolving 1.5 parts of ethyleneglycol monomethyl ether in 4.0 part of water and 1.0 part of the above pulverized HPMCAS was added and dispersed therein in the same manner as in the preceding examples. The results of the solubility test and the disintegration test were as follows.

Solubility in McIlvaine's buffer solutions:
4 to 6 minutes for the solution with a pH of 6.0;
6 to 8 minutes for the solution with a pH of 5.5;

30 to 40 minutes for the solution with a pH of 5.0; and not dissolved within 2 hours in the solution with a pH of 4.5.
Disintegration time:
not disintegrated within 2 hours in the first solution; and
3 to 4 minutes in the second solution.

EXAMPLE 5

The aqueous solution of ethyleneglycol monoethyl ether used as the dispersing medium in the preceding example was replaced with a slightly cloudy solution of 0.1 part of benzyl alcohol and 0.5 part of ethyleneglycol monomethyl ether in 4.0 parts of water, the experimental conditions being the same as in Example 4.

The results of the solubility test and the disintegration test were as follows.
Solubility in McIlvaine's buffer solutions:
4 to 6 minutes for the solution with a pH of 6.0;
5 to 7 minutes for the solution with a pH of 5.5;
20 to 30 minutes for the solution with a pH of 5.0; and not dissolved within 2 hours in the solution with a pH of 4.5.
Disintegration time:
not disintegrated within 2 hours in the first solution; and
2 to 3 minutes in the second solution.

EXAMPLE 6

A hydroxypropylcellulose phthalate having a M.S. value for the hydroxypropoxy groups of 2.97 and a D.S. value for the phthalyl groups of 1.52 was comminuted as frozen in a freezing mill into a fine powder having an average particle diameter of about 20 μm where more than 95% by weight of the particles had a particle diameter of about 40 μm or smaller.

The dispersing medium was prepared by dissolving 0.5 part of glycerin in 4.0 parts of water and 1.0 part of the above pulverized hydroxypropylcellulose phthalate was added and dispersed therein in the same manner as in the preceding examples. The results of the solubility test and the disintegration test were as follows.
Solubility in McIlvaine's buffer solutions:
8 to 10 minutes for the solution with a pH of 6.0;
14 to 20 minutes for the solution with a pH of 5.5; and not dissolved within 2 hours in the solutions with a pH of 5.0 or 4.5.
Disintegration time:
not disintegrated within 2 hours in the first solution; and
5 to 7 minutes in the second solution.

What is claimed is:
1. An aqueous coating composition for providing enteric coating on solid dosage forms which comprises
   (a) water as the dispersing medium;
   (b) an enterosoluble cellulose derivative in the form of a fine powder having a particle size distribution such that more than 95% by weight of the particles have a diameter not exceeding 150 μm and dispersed in said water;
   (c) a plasticizing agent having compatibility with the enterosoluble cellulose derivative boiling at a temperature not lower than 100° C. and contained as dissolved in said water in an amount from 5 to 200% by weight based on the amount of the enterosoluble cellulose derivative; and
   (d) hydroxypropylmethyl cellulose or hydroxyethyl cellulose as a protective colloid.
2. The aqueous coating composition as claimed in claim 1 wherein the boiling point of the plasticizing agent is not lower than 110° C.
3. The aqueous coating composition as claimed in claim 1 wherein the enterosoluble cellulose derivative is selected from the group consisting of cellulose derivatives derived from alkyl ethers of cellulose, hydroxyalkyl ethers of cellulose, monocarboxylic acid esters of cellulose and mixed cellulose ester ethers with a combination of two or more of alkyl, hydroxyalkyl and monocarboxyl groups by mono-esterification with a dibasic or tribasic carboxylic acid.
4. The aqueous coating composition as claimed in claim 1 wherein the enterosoluble cellulose derivative is selected from the group consisting of the monoesters of methylcellulose, ethylcellulose, hydroxyethylcellulose, hydroxypropylcellulose, hydroxybutylcellulose, hydroxyethylethylcellulose, hydroxypropylmethylcellulose, hydroxybutylmethylcellulose, cellulose acetate, cellulose butyrate and cellulose propionate with a dibasic or tribasic carboxylic acid.
5. The aqueous coating composition as claimed in claim 3 or claim 4 wherein the dibasic carboxylic acid is selected from the group consisting of phthalic acid, tetrahydrophthalic acid, maleic acid, succinic acid and glutaric acid.
6. The aqueous coating composition as claimed in claim 3 or claim 4 wherein the tribasic carboxylic acid is trimellitic acid.
7. The aqueous coating composition as claimed in claim 1 wherein the enterosoluble cellulose derivative is selected from the group consisting of hydroxypropylmethylcellulose phthalate, cellulose acetate phthalate, hydroxypropylmethylcellulose acetate succinate and hydroxypropylcellulose phthalate.
8. The aqueous coating composition as claimed in claim 1 wherein the plasticizing agent is selected from the group consisting of monoacetins, diacetins, triacetin, glycerine, ethyleneglycol monomethyl ether, ethyleneglycol monoethyl ether, propyleneglycol, polyethyleneglycol, benzyl alcohol, diacetone alcohol and ethyl lactate.
9. The aqueous coating composition as claimed in claim 1 wherein the amount of the plasticizing agent is in the range from 5 to 200% by weight based on the amount of the enterosoluble cellulose derivative.
10. The aqueous coating composition as claimed in claim 1 wherein the amount of said water as the dispersing medium is in the range from 200 to 2,000% by weight based on the amount of the enterosoluble cellulose derivative.
11. The aqueous coating composition as claimed in claim 1 wherein the amount of the protective colloid is in the range from 0.05 to 5.0% by weight based on the amount of the enterosoluble cellulose derivative.
12. A method for providing enteric coating on solid dosage forms which comprises the steps of
   (a) comminuting an enterosoluble cellulose derivative into a fine powder having an average particle diameter not exceeding 100 μm;
   (b) dispersing the fine powder of the enterosoluble cellulose derivative in an aqueous dispersing medium which is water containing a plasticizing agent having compatibility with the enterosoluble cellulose derivative in an amount from 5 to 200% by weight based on the amount of the enterosoluble cellulose derivative and hydroxypropylmethyl cellulose or hydroxyethyl cellulose as a protective colloid and boiling at a temperature not lower than 100° C. to form an aqueous coating composition; and
   (c) applying the aqueous coating composition to the solid dosage forms followed by drying.

* * * * *